United States Patent [19]
Nelson et al.

[11] Patent Number: 5,265,956
[45] Date of Patent: Nov. 30, 1993

[54] BONE CEMENT MIXING AND LOADING APPARATUS

[75] Inventors: Charles L. Nelson, Santa Clara, Calif.; Michael W. Steffler, Kalamazoo; Douglas L. Tyler, Sr., Paw Paw, both of Mich.

[73] Assignee: Stryker Corporation, Kalamazoo, Mich.

[21] Appl. No.: 769,004

[22] Filed: Sep. 30, 1991

[51] Int. Cl.⁵ .................. B01F 13/06; B01F 15/02; B01F 7/20

[52] U.S. Cl. ................. 366/139; 366/195; 366/196; 366/312; 141/23; 141/27

[58] Field of Search ............ 366/139, 195, 196, 279, 366/309, 312, 313, 326, 328, 329, 131, 181, 184, 188, 194, 349; 141/22, 23, 26, 27, 363, 375, 383

[56] References Cited

U.S. PATENT DOCUMENTS

| | | |
|---|---|---|
| D. 279,499 | 7/1985 | Case . |
| 368,704 | 8/1887 | Bryant ................ 141/27 |
| 414,566 | 11/1889 | Nelleson . |
| 740,751 | 10/1903 | Friedman . |
| 1,023,368 | 4/1912 | Fay . |
| 1,033,667 | 7/1912 | Brown . |
| 1,181,869 | 5/1916 | Gerbing . |
| 1,415,735 | 5/1922 | Trust . |
| 2,095,543 | 10/1937 | Doll ................ 366/130 |
| 2,157,217 | 5/1939 | Rauch ................ 366/242 |
| 2,224,967 | 12/1940 | Kaye . |
| 2,347,195 | 4/1944 | Huff . |
| 2,570,079 | 10/1951 | Spremulli ................ 366/196 |
| 2,696,022 | 12/1954 | Steinbock et al. . |
| 2,973,187 | 2/1961 | Wehmer . |
| 3,290,017 | 12/1966 | Davies et al. ................ 366/130 |
| 3,342,460 | 9/1967 | Bolde . |
| 3,368,592 | 2/1968 | Thiel et al. . |
| 3,635,901 | 1/1972 | Urgesi et al. . |
| 3,739,947 | 6/1973 | Baumann et al. . |
| 3,742,724 | 7/1973 | Carpigiani ................ 366/289 |
| 3,815,878 | 6/1974 | Baskas et al. . |
| 3,907,106 | 9/1975 | Purrmann et al. . |
| 4,015,945 | 4/1977 | Frankel et al. . |
| 4,020,154 | 4/1977 | Perla et al. . |
| 4,069,310 | 1/1978 | Harrison . |
| 4,138,816 | 2/1979 | Warden ................ 366/196 |
| 4,185,072 | 1/1980 | Puderbaugh et al. . |
| 4,208,133 | 6/1980 | Korte-Jungermann ........ 366/130 |
| 4,277,184 | 7/1981 | Solomon . |
| 4,380,399 | 4/1983 | Godat et al. . |
| 4,438,074 | 3/1984 | Wilt . |
| 4,460,279 | 7/1984 | Krasney . |
| 4,462,694 | 7/1984 | Ernster et al. . |
| 4,488,817 | 12/1984 | Uesaka et al. . |
| 4,515,267 | 5/1985 | Welsh . |
| 4,586,823 | 5/1986 | Schöndorfer et al. . |
| 4,676,655 | 6/1987 | Handler ................ 366/289 |
| 4,721,390 | 1/1988 | Lidgren . |
| 4,723,581 | 2/1988 | Staudenrausch ................ 141/27 |
| 4,758,096 | 7/1988 | Gunnarsson . |
| 4,787,751 | 11/1988 | Bakels . |
| 4,854,716 | 8/1989 | Ziemann et al. . |
| 4,961,647 | 10/1990 | Coutts et al. . |
| 4,973,168 | 11/1990 | Chan . |
| 5,015,101 | 5/1991 | Draenert ................ 366/130 |

FOREIGN PATENT DOCUMENTS

| | | |
|---|---|---|
| 1163504 | 2/1964 | Fed. Rep. of Germany ........ 141/26 |
| 1193479 | 5/1965 | Fed. Rep. of Germany . |
| 627769 | 10/1927 | France . |
| 372885 | 12/1963 | Switzerland ................ 141/27 |

Primary Examiner—Harvey C. Hornsby
Assistant Examiner—Randall E. Chin
Attorney, Agent, or Firm—Flynn, Thiel, Boutell & Tanis

[57] ABSTRACT

An apparatus for mixing bone cement and containing the mixed bone cement preparatory to dispensing. The mixing chamber has an outlet for the mixed cement. A cartridge has an inlet releasably coupled to the outlet of the mixing chamber for receiving mixed bone cement therefrom. Structure is provided for moving cement from an upper region of the mixing chamber down into a lower region thereof to mix same and for moving such mixed cement off an inner surface of the mixing chamber and into the cartridge.

16 Claims, 8 Drawing Sheets

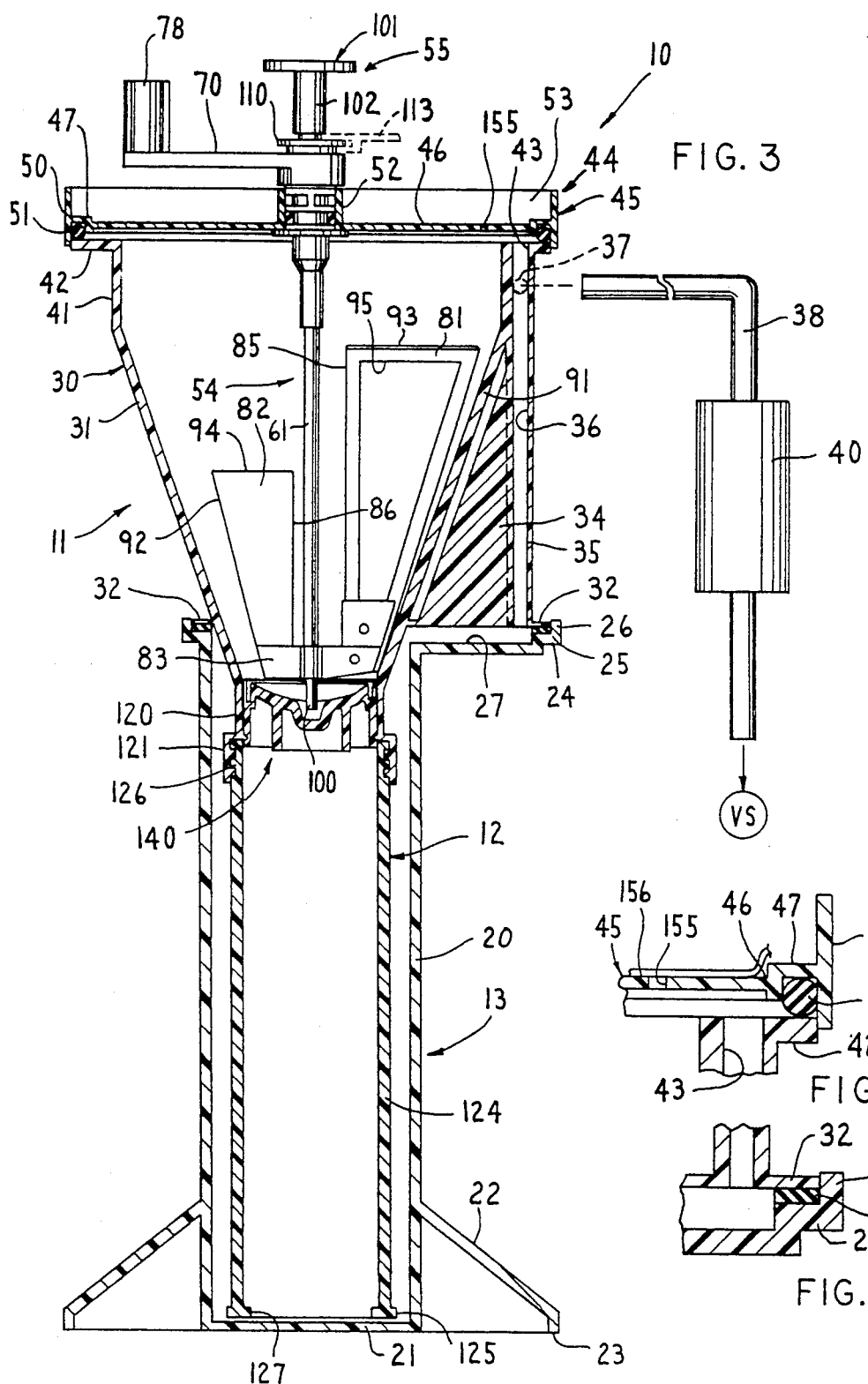

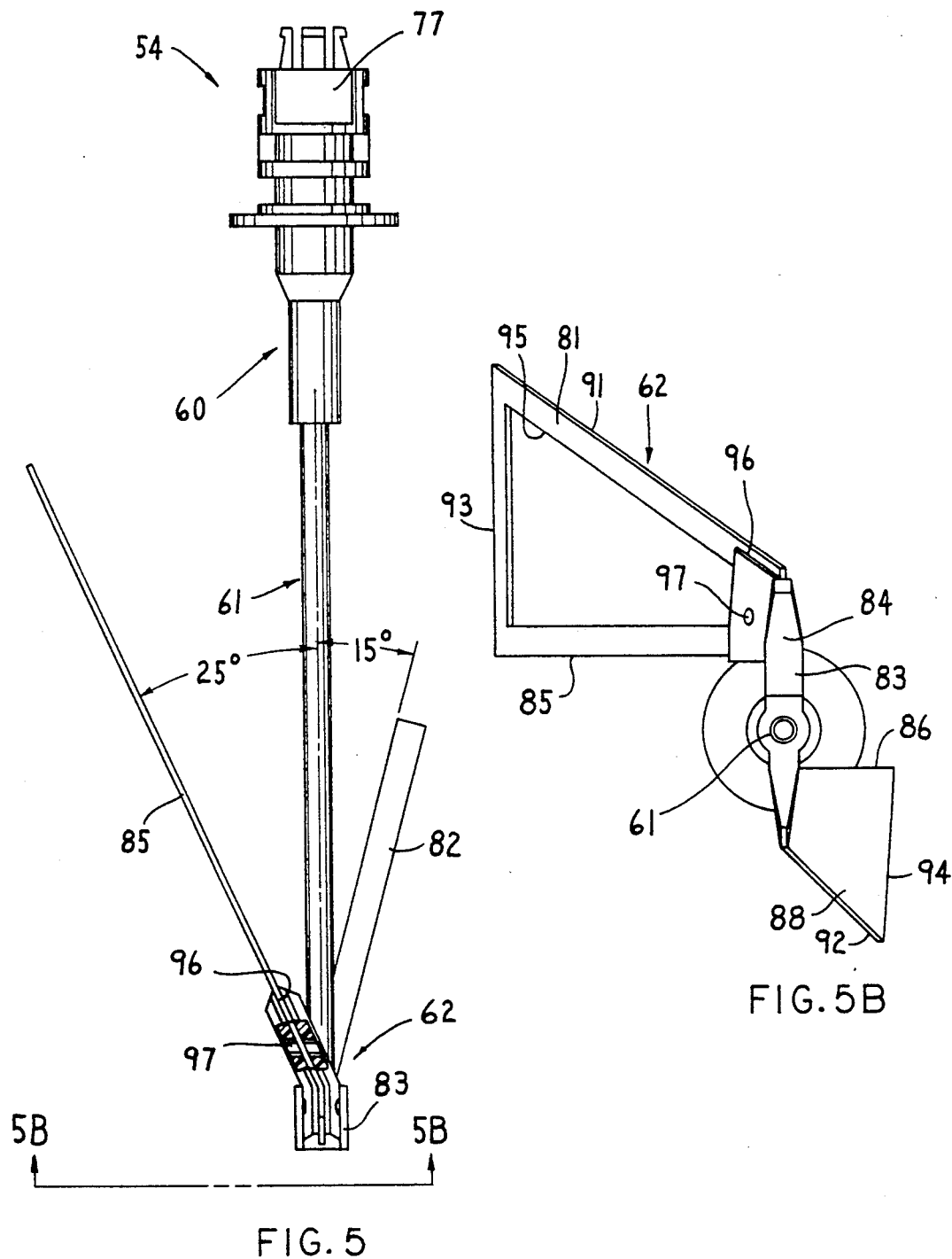

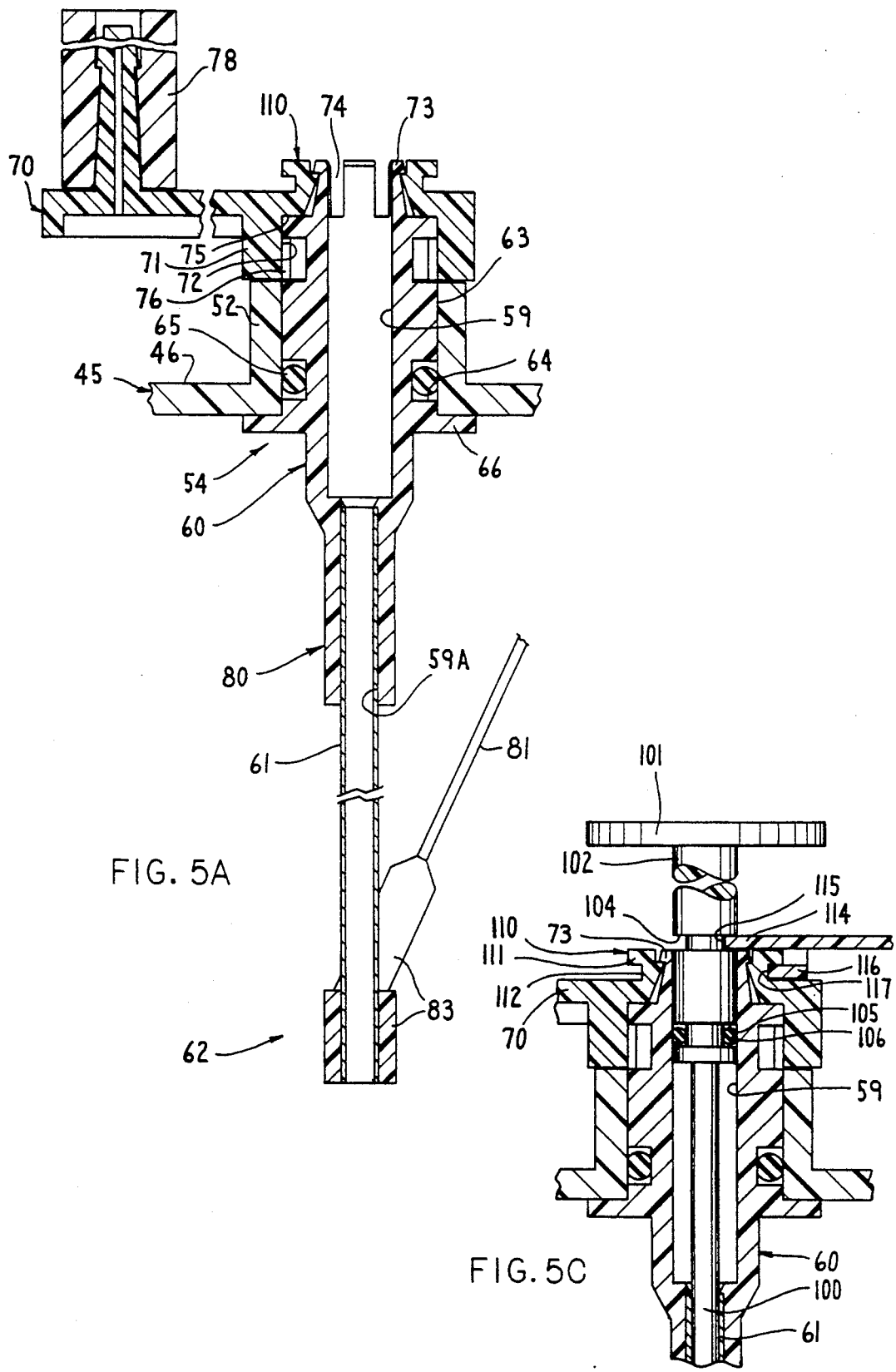

BONE CEMENT MIXING AND LOADING APPARATUS

FIELD OF THE INVENTION

This invention relates to an apparatus for mixing and loading a two-part bone cement of a type suitable for fixing a prosthesis to bone in a surgical patient, and more particularly to such an apparatus for mixing and loading such cement under a partial vacuum (subatmospheric pressure).

BACKGROUND OF THE INVENTION

In orthopedic procedures it is common to use an acrylic bone cement to affix a prosthesis to the bone, for example a hip joint implant to the interior surfaces of the femur. Typically such bone cements are comprised of a liquid monomer and a solid polymer. The solid polymer contains the reaction initiator and is typically a finely divided powder. When the liquid monomer contacts the polymer, a reaction ensues that polymerizes the monomer and cross links the polymer into a high molecular weight polymeric solid. It is known that when the monomer and polymer are mixed under a partial vacuum, the void volume (portion of the volume occupied by air or other gas bubbles) of the resultant high molecular weight polymeric solid is advantageously considerably less than when mixed in air at atmospheric pressure.

Resulting bone cements of this type have been applied to the surgical site in a variety of ways. One way is to use an extrusion device broadly similar to a caulking gun. Typically in prior devices, the mixed bone cement is transferred to a cylindrical cartridge in air at atmospheric pressure or is mixed in the cartridge itself under a partial vacuum. Transfer of the cement into the cartridge in air at atmospheric pressure allows the incorporation of air into the mixture and thus unfortunately can increase the porosity of the cement. On the other hand, when the cement is mixed within the cartridge itself, the surface area available to remove the air from the mixture under partial vacuum is not optimal.

Accordingly, the objects and purposes of the present invention include provision of apparatus intended to overcome these and other drawbacks of prior systems.

A further object of the present invention is to provide adequate surface area to remove air during the mixing process and to transfer the mixed cement into the cartridge while under a partial vacuum.

One aspect of the invention involves an apparatus for mixing bone cement and containing the mixed bone cement preparatory to dispensing, the apparatus comprising a mixing chamber having an outlet for mixed cement, a cartridge having an inlet releasably coupled to the outlet of the mixing chamber for receiving mixed bone cement therefrom, and means for moving cement from an upper region of the mixing chamber down into a lower region thereof to mix same and for moving such mixed cement off an inner surface of the mixing chamber and into the cartridge.

Other objects and purposes of the invention will be apparent to persons acquainted with apparatus of this general type upon reading the following description and inspecting the accompanying drawings.

BRIEF DESCRIPTION OF THE DRAWINGS

FIG. 3 is an enlarged central cross-sectional view of the FIG. 2 apparatus with the piston and push rod in their upper (preloading) positions;

FIG. 3B is an enlarged fragment of FIG. 3 showing the seal between the lid assembly and the top of the funnel;

FIG. 3C is an enlarged fragment of FIG. 3 showing the seal between the funnel and the vacuum shroud;

FIG. 5 is an enlarged side elevational view of the shaft assembly, substantially as taken along the line 5—5 of FIG. 2 and showing same edgewise;

FIG. 5A is a fragmentary enlarged central cross-sectional view of the shaft assembly substantially taken on the line 5A—5A of FIG. 4 and with the crank handle rotated 90° clockwise as seen from the top of FIG. 4, and with the push rod removed;

FIG. 5B is a bottom view of the shaft assembly substantially taken on the line 5B—5B of FIG. 5;

FIG. 5C is a view similar to FIG. 5A but with the push rod in place; and

DETAILED DESCRIPTION

Figure 1:
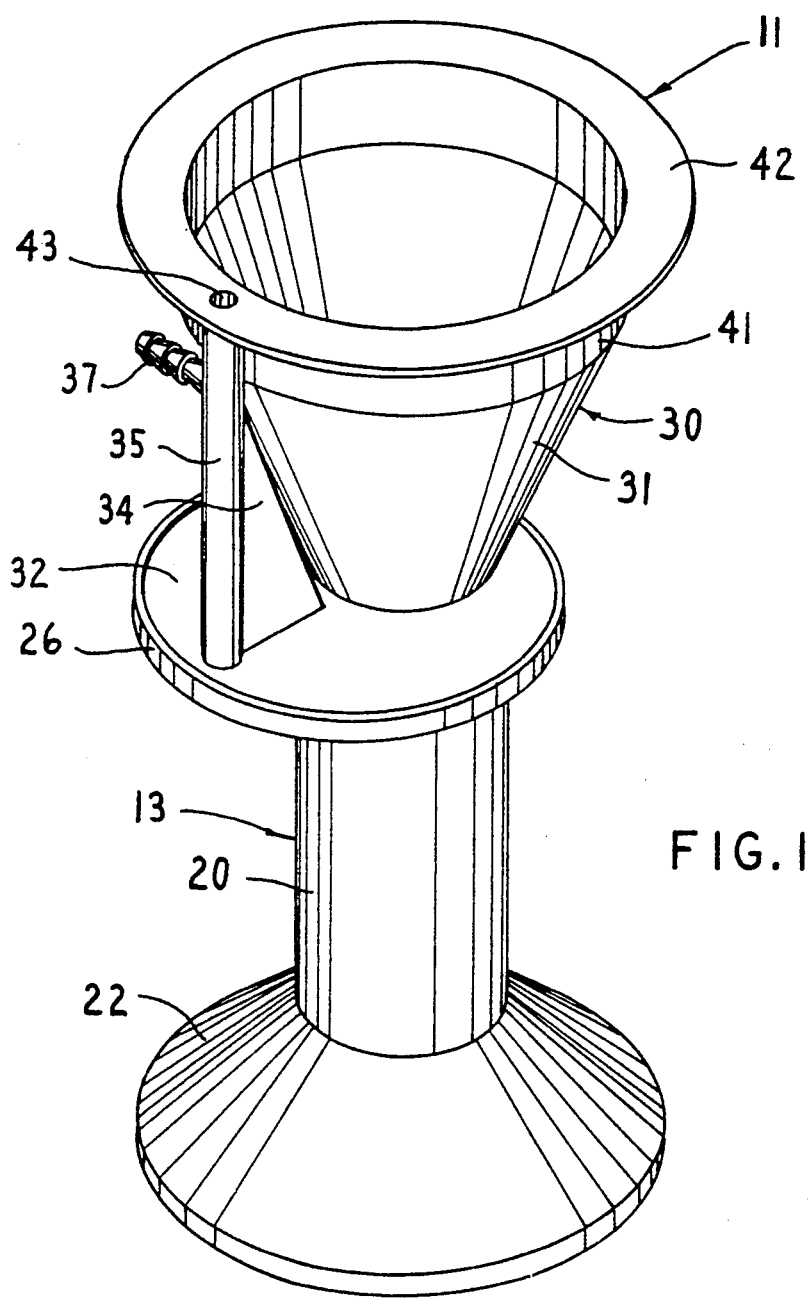
FIG. 1 is a pictorial view of a mixing and loading apparatus embodying the invention, with its lid assembly removed from atop the mixing chamber.

A bone cement mixing and loading apparatus 10 (FIGS. 1 and 2) embodying the invention comprises a mixing chamber 11 and a cartridge 12 located below the mixing chamber 11 for receiving mixed bone cement therefrom. A vacuum shroud 13 (FIG. 3) supports the mixing chamber and cartridge as hereafter discussed.

The vacuum shroud 13 comprises an upstanding cylindrical casing 20 having a closed bottom 21. The bottom portion of the casing 20 has a downwardly and outwardly flared, substantially conical, skirt 22. The skirt 22 preferably protrudes slightly below the casing 20. The bottom edge 23 of the skirt 22 supports the apparatus 10 on a table or the like during mixing and loading. Preferably the diameter of the skirt 22 is at least approximately equal to the maximum diameter of the mixing chamber to support same in a stable manner and to minimize the effect of horizontal moments upon the apparatus 10 during use.

The upper end of the vacuum shroud casing 20 is open upward and surrounded by a circular radial flange 24. The center line of the outside diameter of the radial flange 24 is not coaxial with the cylindrical casing 20 but rather is offset sidewardly (to the right in FIG. 3). In the embodiment shown, the rightward (FIG. 3) portion of the radial flange 24 extends to the right about as far as the widest point on the mixing chamber 11. A flat, resilient, annular seal ring 25 seats atop the radially outer portion of the radial flange 24 and is laterally fixed by a perimeter ridge 26 fixedly upstanding from the perimeter of the radial flange 24. A depression 27 in the top of the radial flange 26 extends radially inward from the seal 25 to communicate with the top of the cylindrical casing 20.

The mixing chamber 11 comprises an open-topped, downwardly converging funnel 30 (FIGS. 2 and 3) whose sidewall is of frusto-conical shape intermediate its upper and lower ends and through the major portion of its height. In the preferred embodiment shown, the frusto-conical sidewall 31 of the funnel 30 is angled divergently upwardly at about 15° to 25° (here about 20°) to the vertical. A radial flange 32 extends fixedly and horizontally outward from the frusto-conical sidewall 31 of the funnel 30, adjacent but spaced above the lower end of such sidewall 31. The flange 32 is annular and surrounds the bottom portion of the funnel 30 but is eccentrically offset to the right thereof in FIGS. 2 and 3, in the same manner as the radial flange 24 on the top of the vacuum shroud 13. The funnel flange 32 is sized and located laterally to seat in a circumferentially continuous manner on the seal ring 25. The upper portion of the perimeter ridge 26 of the vacuum shroud 13 closely surrounds the funnel flange 32 to positively locate it horizontally, and radially about the central axis of the funnel 30.

The upstanding central axis of the funnel 30 and the upstanding central axis of the vacuum shroud cylindrical casing 20 are coaxial, as seen in FIG. 3, when the funnel flange 32 is properly seated on the seal ring 25 and vacuum shroud radial flange 24.

Figure 2:
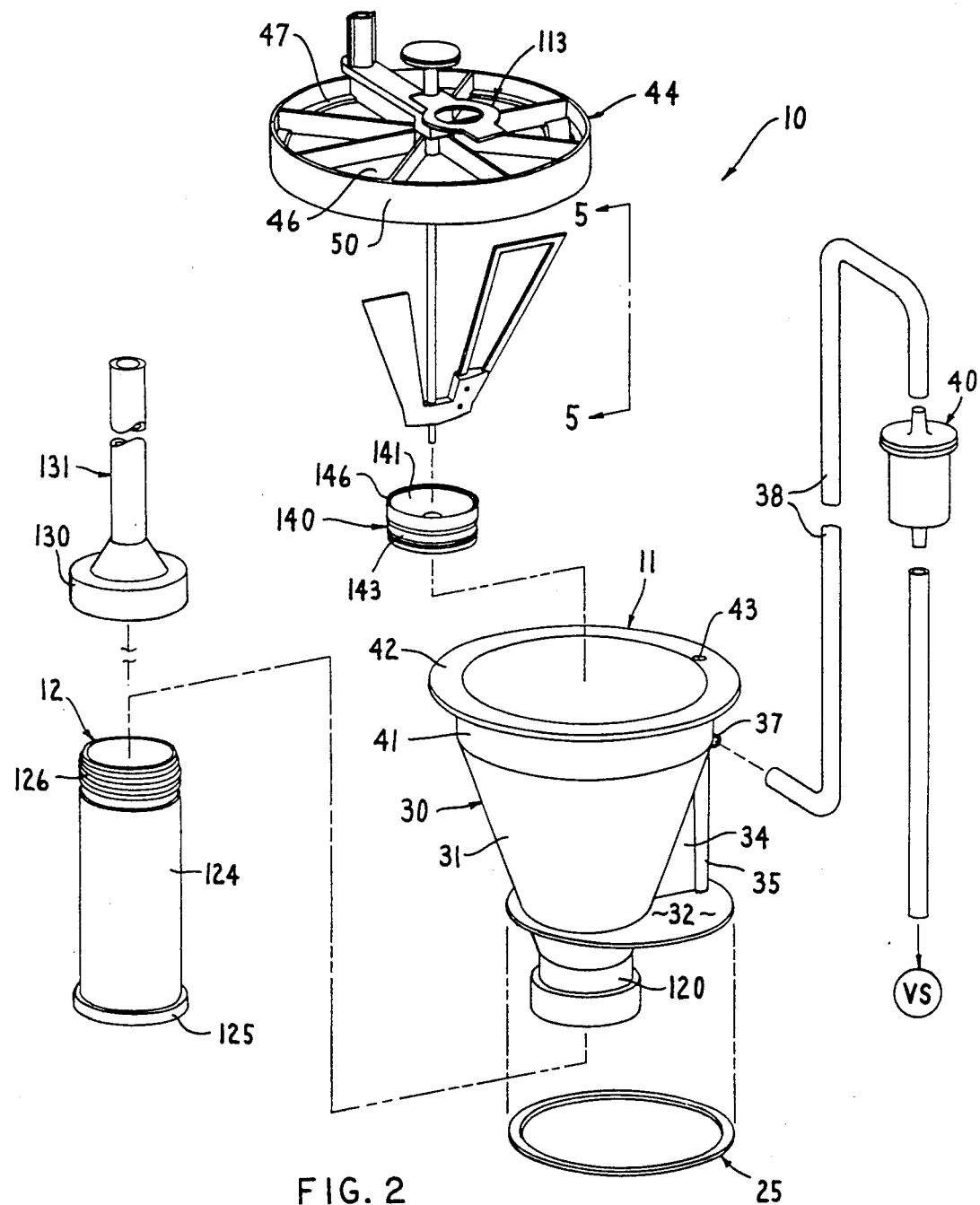
FIG. 2 is an exploded pictorial view of the apparatus of FIG. 1 but including the lid assembly, and a cartridge to be loaded with bone cement and an example of an outlet nozzle alternatively securable to the cartridge.

An upstanding web 34 extends rightward from the funnel 30 (as seen in FIG. 2 and 3) and extends upward from the top of the flange 32. The upstanding radially outer edge 35 of the web 34 is thickened and houses a fluidic communicative passage 36 which is open at its bottom to the depression 27 and is open at its top flush with the top of the funnel 30. The opening of the passage 36 is larger at the top of the funnel 30 than at its bottom which leads to the depression 27. This creates a fluidic restriction at its bottom 27 which creates a pressure drop. This pressure drop in turn forces the conical mixing chamber to be vented to atmospheric pressure before the shroud. As partially seen in FIG. 2 and indicated by broken lines in FIG. 3, a hollow stub 37 communicates with the passage 36 intermediate its ends for connection thereto of a vacuum tube 38 leading through an activated carbon filter 40 to a conventional vacuum source VS.

In the embodiment shown, the top of the funnel 30 has a relatively short cylindrical top portion 41 extending up from the conical sidewall 31 and surrounded by a horizontal radially outward extending annular flange 42. The vertical passage 36 opens up through the top of the annular flange 42, leaving a hole 43 in the top of the flange. The flange 42 is preferably coaxial with the funnel 30.

A lid assembly 44 includes a lid 45 including a horizontal wall 46 (FIGS. 2 and 3) having an upstepped perimeter 47 bounded by a cylindrical perimeter flange 50 having portions extending both above and below the horizontal wall 46 and upstepped perimeter 47. The depending portion of the perimeter flange 50 and upstepped perimeter 47 cooperate with the funnel top flange 42 to trap therebetween a resilient vacuum seal ring, here an O-ring, 51. The bottom portion of the cylindrical perimeter flange 50 snugly but vertically slidably surrounds the funnel top flange 42 to prevent sideways displacement of the lid assembly 44 with respect to the funnel 30.

Figure 6:
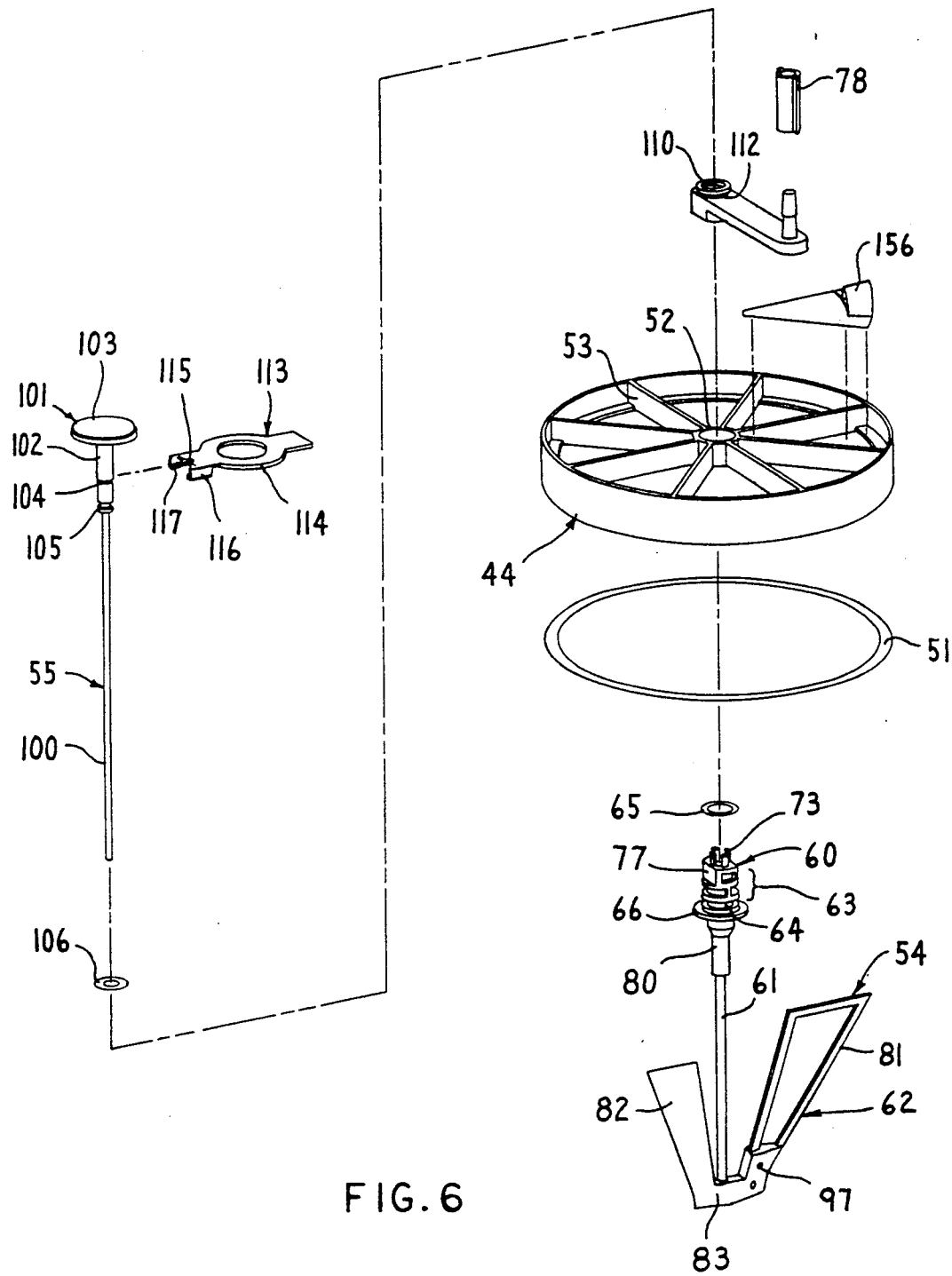
FIG. 6 is an exploded pictorial view of the cover and rotor portions of FIG. 2.

A cylindrical hub is fixedly upstanding from the top of the horizontal wall 46 of the lid in coaxial relation therewith, as seen in FIGS. 3 and 6. Platelike spokes 53 (FIGS. 2 and 6) radiate from the hub 52 out to the perimeter flange 50 to increase the rigidity of the horizontal wall 46 of the lid 45.

The hub 52 vertically and rotatably supports a hollow shaft assembly 54 (FIGS. 3 and 6) pendent coaxially therefrom. The shaft assembly 54 depends into the funnel 30 when the lid assembly 44 closes the top of the funnel 30 as seen in FIG. 3. The shaft assembly 54 in turn coaxially slidably supports therein a push rod 55. Seals 65 and 106 hereafter described are interposed between the hub 52, shaft assembly 54 and push rod 55 to prevent air leakage therepast into the funnel 30.

The shaft assembly 54 (FIG. 6) comprises a hollow tubular head 60 (FIG. 6) from which fixedly and coaxially depends a rigid tube 61. The head 60 has an up-opening bore 59 (FIG. 5A) which steps down to a downward opening coaxial reduced diameter bore 59A which in turn fixedly receives coaxially therein the upper end of the rigid tube 61. A rotor 62 is fixed on the lower end of the tube 61.

The head 60 (FIGS. 5A and 6) includes a generally cylindrical upper portion 63 rotatably supported within the lid hub 52. An annular groove 64 low on the cylindrical upper portion 63 receives a resilient annular seal, here an O-ring, 65 which bears sealingly on the interior of the lid hub 52 and creates a vacuum tight seal between the shaft assembly 54 and lid 45 to prevent passage of air therepast into the mixing chamber 11. A radially outwardly extending annular flange 66 at the bottom of the cylindrical upper portion 63 of the head bears on the underside of the horizontal wall 46 of the lid 45 to block upward motion of the shaft assembly 54 with respect to the lid 45.

A manually rotatable crank handle 70 (FIG. 5A) is fixed to the top of the shaft head 60 and rests atop the lid hub 52 to prevent the shaft assembly 54 from dropping downward with respect to the lid 45. More particularly, the handle 70 includes an upstanding hollow boss 71 at one end thereof which telescopes over the top of the head 60. The boss 71 has a central through opening 72 which receives the upper end of the head 60. Circumferentially spaced, radially outwardly hooked fingers 73 at the upper end of the head 60 are resiliently radially outwardly biased. The outwardly hooked fingers 73 snap over an upward facing annular step 74 located in and near the top of the central through opening 72 of the handle boss 71, to prevent the handle 70 from being lifted off the top of the shaft head 60. The bottom of the handle boss 71 rests rotatably atop the lid hub 52 so as to prevent the shaft assembly 54 from dropping down through the lid 45. In this way the shaft assembly 54 is rotatably supported by the lid 45 and is axially fixed with respect thereto.

The handle boss 71 has a downward facing step 75 spaced below the step 74 and which rests rotatably atop the generally cylindrical upper portion 63 of the shaft head 60. Thus, the handle is vertically fixed between the top of the generally cylindrical upper portion 63 of the head and the radially outwardly hooked fingers 73 spaced thereabove. The end of the crank handle remote from the handle boss 71 rotatably supports an upstanding, hand engageable knob 78 orbitable to rotate the shaft assembly 54.

Rotation of the handle 70 positively rotates the shaft assembly 54. In the embodiment shown, this is accomplished by bearing of a pair of diametrally opposed flats 76 within the lower portion of the handle boss through opening 72 on a corresponding pair of diametrally opposed flats 77 (FIGS. 5 and 6) on the upper part of the generally cylindrical upper portion 63 of the head 60.

The shaft assembly head 60 (FIG. 5A) includes a coaxial stepped tubular skirt 80 (FIGS. 5A and 6) which extends below the flange 66 and hence below the lid 45. The skirt 80 is thus located within the mixing chamber 11 when the lid assembly and shaft assembly are located atop the funnel 30 in the normal position of use shown in FIG. 3. The rigid tube 61 (FIG. 5A) is fixedly telescoped at its upper end in the lower portion of the skirt 80 for rigid coaxial depending fixation of the tube 61 to the bottom of the head 60.

The rotor 62 is fixed to the bottom of the tube 61 and comprises an auger 81 (FIGS. 5A and 6), a paddle 82 and a base 83 interconnecting the auger 81 and paddle 82 to the bottom of the tube 61 in a rigid manner.

As seen in FIG. 3, the base 83 extends down to about the bottom of the conical sidewall 31 of the funnel 30. The auger 81 and paddle 82 extend generally upward from the base 83 into the midportion of the funnel 30. The auger 81 extends up to substantially the top of the conical sidewall 31 and the paddle 82 extending to about half that height. As seen in FIGS. 5, 5B and 6, the auger 81 and paddle 82 are inclined upward in opposite directions away from the diametral plane 84 (FIG. 5B) of the base, here at about 25° and 15° respectively, as seen in FIG. 5.

The auger 81 and paddle 82 are thin platelike elements of truncated triangular perimeter shape (the bottom point of the triangle being cut off in each instance). As seen in FIG. 3, the auger 81 and paddle 82 have generally upstanding radially inner edges 85 and 86 respectively (FIGS. 3 and 5B) which lie in planes parallel to the upstanding longitudinal axis of the shaft tube 61, and are respectively radially spaced from and radially closely adjacent to the tube 61. The auger 81 and paddle 82 have generally upstanding radially outer edges 91 and 92 respectively, which angle up and out substantially at the same angle as the upward and outward angling conical sidewall 31 of the funnel 30. The auger outer edge 91 bears against the funnel sidewall 31 to wipe therealong in response to rotation of the handle 70. On the other hand, the outer edge 92 of the paddle 82 is spaced radially inward from the funnel sidewall 31. In the preferred embodiment shown, the top edges 93 and 94 of the auger 81 and paddle 82 are substantially horizontal.

Whereas the paddle 82 is solid, the auger 81 has a large central opening 95 (which indeed here is bigger than the paddle 82). The auger central opening 95 has edges which are approximately parallel, and are inwardly spaced from the top, bottom and side perimeter edges (e.g. 93, 85 and 91) of the auger 81.

In the embodiment shown, the base 83 and paddle 92 are integrally molded of a suitable rigid plastics material, whereas the auger 81 is of substantially rigid, but elastically bendable, stainless steel sheet material with its bottom end portion fixed in a slot 96 (FIG. 5) in the base 83. In the preferred embodiment shown, the auger is insert molded to the base 83. The auger is rigidly fixed by plastic flowing through holes in the auger and solidifying as seen at 97. The central opening 95 in the platelike auger 81 makes the auger 81 more flexible and also increases the number of edges engageable with cement components to be mixed so as to increase the amount of mixing per rotation of the handle.

The radially outer edge 91 of the preferred auger 81 shown is, in the relaxed planar condition of the auger, straight. On the other hand, with the plane of the auger tilted at 25° to a diametral plane of the funnel 30, the line of intersection of the plane of the auger with the interior surface of the conical funnel sidewall 31 would be curved. However, the flexibility of the sheet material of the auger 81 allows it to bend and thereby define a curved, rather than planar, sheet as it rotatably mixes cement within the funnel 30. The curvalinear bending of the sheet material of the auger 81 accordingly causes the radially outer edge 91 thereof to be similarly curvalinearly bent, so that the auger radially outer edge 91, along its entire height, closely engages the interior surface of the conical sidewall 31 of the funnel 30 to wipe cement therefrom.

The push rod 55 (FIGS. 3, 5C and 6) comprises a circular cross section, cylindrical rod element 100. The push rod 55 fixedly, coaxially tops the rod element 100 with a head 101 comprising a shank 102 fixed on the upper end of the rod element 100 and topped by a fixed, integral and radially outwardly extending, hand depressible button 103. The shank 102 has upper and lower annular grooves 104 and 105 (FIGS. 5C and 6), respectively near the mid-portion thereof and near the lower end thereof. The push rod is installed in the hollow shaft assembly 54 by inserting the lower end of the rod element 100 downward into the up-opening bore 59 (FIG. 5A) of the head 60.

The push rod 55 has first and second operating positions (respective upper and lower operating positions) within the shaft assembly 54.

The lower annular groove 105 carries a resilient annular seal, here an O-ring, 106. In the first, up position of the push rod 55 shown in solid lines in FIG. 5C, the O-ring 106 engages the upper part of the upper bore 59 of the cylindrical upper portion 63 of the shaft head 60 and creates a vacuum-tight seal between the shaft assembly 54 and push rod 55. The rod element 100 of the push rod 55 extends snugly but slidably down into the rigid tube 61 of the shaft assembly. In this upper position of the push rod, its upper annular groove 104 is exposed immediately above the top of the handle 70, which is flush with or extends slightly above the tops of the fingers 73. More particularly, the top of the handle 70 in the portion thereof surrounding the fingers 73, is formed by an upstanding annular projection 110 (FIGS. 3, 5A and 6) upstanding from the major length of the handle 70 and defined by a radially outwardly extending annular flange 111 overlying a coaxial annular groove 112.

A retaining clip 113 is, in the preferred embodiment shown, used to lock the push rod 55 in its upper position shown in solid lines in FIG. 5C, during mixing and prior to loading of the mixed cement downward into the cartridge 12. The clip 113 here comprises a platelike body 114 (FIG. 6) of any convenient shape to be gripped by the fingers of the user. The leftward (FIG. 6) end of the platelike body 114 has a depending portion forming a leftward opening boxlike rectangular cross section sleeve 116 integral with and depending from the plane of the body 114. Notches 115 and 117 open leftward from the upper and lower walls of the boxlike sleeve 116 so as to allow the upper and lower walls of the boxlike sleeve 116 to be leftwardly received in the annular grooves 104 and 112 respectively in the push rod 55 and handle annular projection 110, to thereby engage in the retainer clip notches 115 and 117 the material of the push rod 55 and handle 70. With the retainer clip 113 thus in place, as shown in solid lines in FIG. 5C, the push rod 55 cannot be pushed downward out of its upper position shown nor be inadvertently pushed upwardly to unseat the O-ring resilient vacuum seal 106. Pulling the retainer clip 113 rightwardly (FIG. 5C) out of contact with the push rod 55 and handle 70 allows the push rod 55 to be pushed downward by the operator out of its position of FIGS. 3 and 5C and into its lower position of FIG. 4. Thus, after mixing is completed and it is desired to allow the push rod to be moved downward to its lower position in FIG. 4, the operator merely grips the clip 114 in his fingers and pulls same radially out of engagement with the push rod 55. The push rod 55 is then free to be pushed downwardly farther into the shaft assembly into its lower position of FIG. 4.

Figure 3A:
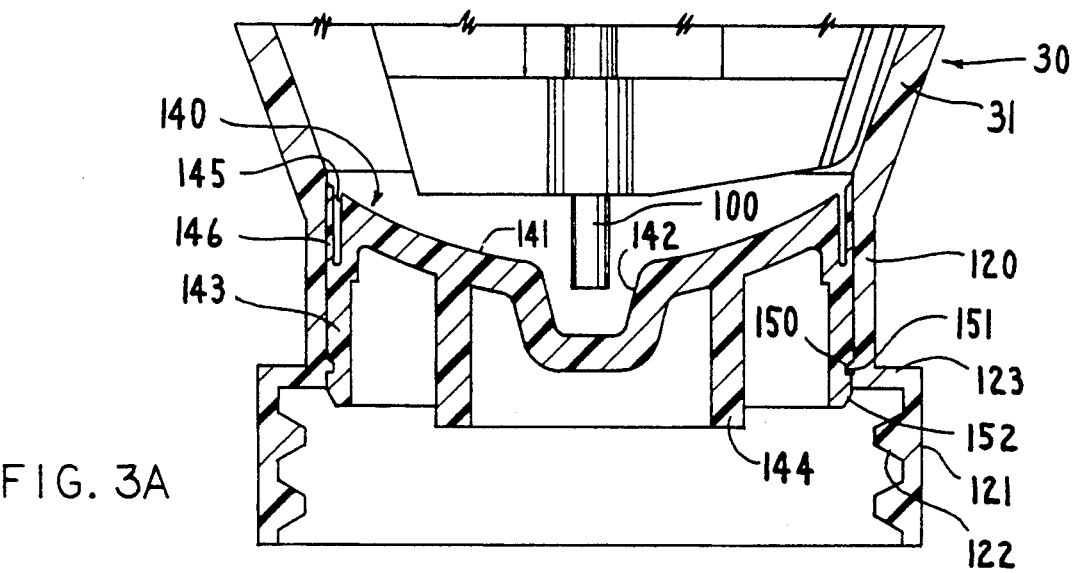
FIG. 3A is an enlarged fragment of FIG. 3 showing the piston at the lower end of the funnel.

The funnel 30 (FIGS. 3 and 3A) has a cylindrical outlet portion 120 integrally and coaxially dependent from the bottom of the conical portion 31. The bottom of the mixing chamber 11 is a threaded connector sleeve 121 which integrally and coaxially depends from the cylindrical outlet portion 120, is radially enlarged from the cylindrical outlet portion 120 and has internal threads 122 (FIG. 3A). The threaded connector sleeve 121 at its top integrally connects to the coaxial, smaller diameter cylindrical outlet portion 120 by a radially inward extending flange 123.

As seen in FIGS. 2 and 3, the cartridge 12 comprises a hollow tube 124, open at its upper and lower ends, and provided at its lower end with a radially outwardly extending flange 125 for removable connection to a gunlike cement ejector (not shown). Various types of gunlike cement ejectors are known and a preferred one is disclosed in corresponding U.S. application Ser. No. 07/769,003 assigned to the assignee of the present invention. The flange 125 can thus be called a gun mount flange. The cartridge 12 also has a radially inwardly extending flange 127 (FIG. 4) at the bottom of the tube 124.

The upper end of the cartridge tube 124 is externally threaded at 126. The external threads 126 serve two purposes.

First, during loading of the cartridge 12 with mixed cement, as hereafter discussed, the threaded upper end 126 of the cartridge tube 124 is fixedly but releasably coaxially threaded up into the internal threads 122 of the threaded connection sleeve 121 and against the flange 123, to fix the cartridge 12 to the bottom of the mixing chamber 11 for filling with cement mixture. The interior walls of the funnel cylindrical outlet portion 120 and cartridge tube 124 are of the same diameter and axially abut, so as to axially smoothly continue one into the other without discontinuity, for smooth filling of the cartridge with mixed cement from the funnel.

The second purpose served by the threads 126 on the top of the cartridge 12 is to threadedly receive, after the cartridge 12 is filled with cement mixture and removed from the mixing apparatus 10, the internally threaded end 130 of a cement injection nozzle of any convenient type and represented in FIG. 2 by way of example at 131. It will be understood that a variety of injector nozzles 131 can be fitted to the threaded end 126 of the cartridge 12.

If desired, the exterior surface of the cartridge 12 can be provided with axially extending and/or circumferentially extending reinforcing ribs, not shown, to reinforce the cartridge against internal pressure applied to the mixed cement therein during dispensing into a surgical site.

A piston 140 (FIGS. 2, 3 and 3A) here comprises a circular, hockey puck-shaped member comprising an upwardly concavely curved top 141 (FIG. 3A) having a relatively narrow central depression 142. The diameter of the depression 142 somewhat exceeds the diameter of the bottom of the rod element 100 and is adapted to receive the latter therein as hereafter discussed. The piston 140 further includes a substantially cylindrical peripheral wall 143 depending from the periphery of the top 141 and an annular cylindrical reinforcing flange 144 depending from the top 141 in radially spaced relation between the depression 142 and peripheral wall 143. The upper portion (for example the upper ¼ to ⅓) of the piston peripheral wall 143 is separated from the central portion of the piston 140 by a narrow, upfacing annular groove 145 and thereby forms an upstanding and somewhat radially outwardly biased annular feather seal 146. The annular feather seal 146 pushes radially outward against, and thus seals against, the surrounding internal cylindrical surface of the lower end portion of the funnel 30 in the upper position of the piston shown in FIG. 3A. It will be understood that the upstanding annular feather seal 146 similarly bears resiliently and sealingly against the interior surface of the cartridge tube 124 after the piston has been pushed down into the cartridge 12 (see for example FIG. 4), as hereafter described.

The downward and radially outward pressure of fluid cement components and mixed cement, against the top of the piston 140, presses the feather seal 146 even more firmly radially out against the surrounding interior walls of the funnel bottom portion and (later) the cartridge tube, to further improve the effectiveness of the feather seal 146. Nevertheless, the orientation of the feather seal 146 allows it to slide easily downward, in a wiping manner, along such surrounding walls, without any tendency to catch or snag, so as not to interfere with easy downward sliding of the piston 140.

The piston 140 is initially positioned in its FIG. 3A position, namely in the cylindrical outlet 120 of the mixing chamber 11. The piston 140 is resiliently held in this position by a resilient detent here comprising an annular bead 150 radially inward extending from the interior face of the outlet 120, which bead 150 snaps into a correspondingly shaped outwardly opening annular groove 151 in the bottom half of the cylindrical sidewall 143 of the piston 140. In this position, the piston 140, with its peripheral feather seal 146, plugs the bottom of the mixing chamber 11 prior to and during mixing so that the cement components cannot escape from the funnel 30 downward into the cartridge 12. On the other hand, after mixing is completed, a modest downward pressure, manually exerted by the user on the push rod 55, overcomes the resilient detent at 150, 151 and displaces the piston 140 downward past the flange 150, out of engagement with the funnel 30 and into the top of the cartridge tube 124. The bead 150 and groove 151 have radially inward and downward sloped top surfaces which cooperatively block accidental dropping of the piston 140 during mixing but allow intended downward displacement of the piston by the user. This geometry thus facilitates the transition of the piston from the seat in the bowl down into the cartridge. On the other hand, the bead 150 and groove 151 have bottom portions with a square edge which prevents the piston from moving upwards. The square edge greatly increases the force required to vertically move the piston upward. Therefore, force required to move the piston vertically upward is greater than the force to move the piston vertically downward.

The bottom outer edge of the piston 140 is preferably chamfered at 152 to facilitate downward motion of the piston into the outlet portion of the mixing chamber 11 and thereafter into the cartridge 12.

The horizontal wall 46 of the lid 45 at a location spaced laterally from the hub 52, spokes 53 and perimeter flange 50 is provided with a small through hole 155 (FIG. 3B) which is normally covered and sealed by a vacuum release label 156.

In general, the components of the above-described apparatus 10 are of suitable rigid plastics materials. The piston 140 is preferably of molded high density polyethylene with a thin enough cross section in its annular feather seal 146 as to allow resilient inward bending thereof by the surrounding lower cylindrical portion 120 of the funnel as to create a seal therebetween as seen in FIG. 3A. The rigid tube 61, auger 81 and rivets 97 are preferably of stainless steel. The annular seals 25 and 51 are of a conventional resilient material, such as rubber or neoprene, as are the O-rings 65 and 106 (FIG. 6) which seal between the lid 44, shaft assembly 54 and push rod 55. The vacuum release label 156 is a pliable, adhesive tape-like member.

OPERATION

The apparatus 10 is intended to mix a two-part bone cement under a partial vacuum and, continuing under the same partial vacuum, to displace the mixed cement into a dispensing cartridge atop a piston therein for subsequent ejection from the cartridge e.g. into the opened top of a femur prior to inserting the stem of a hip joint replacement.

The lid assembly 44 can be assembled as follows. The upper portion 63 (FIG. 5A) of the shaft assembly 54 is inserted up through the hub 52 of the lid 45 until the shaft flange 66 abuts the bottom of the lid horizontal wall 46. The O-ring 65, in the shaft groove 64, thus forms a vacuum seal with the interior of the lid hub 52. Thereafter, the radially inner end of the crank handle 70, with its upstanding annular projection 110, is snapped over the fingers 73 at the upper end of the shaft upper portion 63 to axially lock together the handle 70, shaft head 60 and lid 45. The handle 70 will receive the upper end of the shaft assembly only with the corresponding sets of flats 76 and 77 opposed so that rotation of the handle 70 positively rotates the shaft assembly. The preassembled shaft assembly includes not only the head 60, but also the depending tube 61 and rotor 62 with its auger 81 and paddle 82 (FIG. 3).

The push rod 55, with the O-ring 106 installed in its lower annular groove 105, is dropped down into the open top of the shaft assembly 54. More particularly the depending rod element 100 is dropped down into the open top of the shaft assembly 54, through the bore 59 and tube 61. The shank 102 of the push rod 55 (FIG. 5C) is pushed downward into the shaft upper bore 59 to the groove 104, leaving the latter exposed. The retainer clip 113 is installed in its upper annular groove 104 of the push rod 55 and in the annular groove 112 (FIG. 5C) of the upward annular projection 110 at the radially inner end of the handle, thus blocking further downward entry of the push rod 55 into the shaft assembly 54. In this position, the push rod O-ring 106 bears sealingly against the surrounding upper shaft bore 59 to effect a vacuum seal between the push rod 55 and shaft assembly 54. Also in this position, the bottom end of the rod element 100 is exposed to a small extent below the shaft assembly, to an extent that will leave it close spaced above the depression in the top of the piston 140, as shown in FIG. 3.

The piston 140 is dropped down through the open top of the funnel 30 and pushed down into the cylindrical outlet portion thereof until the annular bead 150 snaps into the annular groove 151 in the piston so as to fixedly close the bottom of the mixing chamber 11. The annular feather seal 146 seals against the cylindrical interior wall at the bottom of the funnel 30 as seen in FIG. 3.

A cartridge tube 124 (FIG. 3) is threaded at its upper end into the threaded connector sleeve 121 at the bottom of the funnel 30 in a snug manner.

The joined funnel 30 and cartridge 12 are dropped downward onto the open top of the vacuum shroud 13, with the cartridge 124 loosely entering the cylindrical casing 20 of the vacuum shroud and the funnel radial flange 32 resting atop the seal ring 25 which in turn rests atop the upfacing radial flange 24 at the top of the vacuum shroud 13.

The cement components are poured into the open top end of the funnel 30. A typical bone cement is, for example, an acrylic cement comprised of a liquid monomer and a solid polymer. The solid polymer contains the reaction initiator and is typically a finely divided powder. When the monomer contacts the polymer a reaction ensues that polymerizes the monomer and crosslinks the polymer into a high molecular weight polymeric material. Either the liquid monomer or solid particulate polymer can be added first. The piston 140 in its FIG. 3 position prevents leakage of either downward out of the bottom of the funnel 30 and into the upstanding cartridge tube 124. In the following discussion, it is assumed, by way of example, that the liquid monomer is added first and thus pools atop the piston 140 in the bottom of the funnel 30.

Once both components of the cement have been dropped into the top of the funnel 30, the lid, now carrying the shaft assembly 54 and push rod 55, is placed atop the top flange 42 of the mixing chamber 11 (FIG. 3), with the O-ring 51 axially interposed therebetween for vacuum sealing therebetween. Such locates the lower portion of the shaft assembly 54, notably the tube 61, auger 81, paddle 82 and base 83, within the conical portion 31 of the funnel 30, the base 83 and push rod bottom end lying slightly above the piston 140.

At this point, the vacuum source VS can be turned on, or connected to the stub 37 (FIG. 3). The vacuum source draws air and other gases from the interior of the funnel 30, through the hole 43 in the flange 42, and from inside the lower portion of the cartridge tube 124 and within the vacuum shroud cylindrical casing 20 upward through the depression 27 and the lower portion of passage 36, so as to place these areas under a partial vacuum (subatmospheric pressure). The filter 40 absorbs noxious reaction gases from mixing of the cement components and drawn from the mixing chamber 11. Atmospheric pressure outside the apparatus 10, being greater than the partial vacuum in the interior of the funnel 30 and within the vacuum shroud 13, presses the lid 45 and the top of the vacuum shroud 13 in tight axially sandwiching relationship against the annular seals 51 and 25 and therethrough against the top and bottom ends of the funnel 30 to block air leakage into the interior of the funnel 30 and vacuum shroud 13 so as to maintain a partial vacuum therein during mixing of the cement components. This pressure difference, between the higher outside atmospheric pressure and the lower inside subatmospheric pressure (partial vacuum), rigidly fixes axially together the lid assembly 44, the mixing chamber 11, and vacuum shroud 13, without need for any other fastening means, and to the extent required to enable mixing of the cement and loading of the mixed cement into the cartridge as hereafter discussed in more detail. The O-rings 65 and 106 maintain a vacuum seal between and prevent air leakage between the lid 45, shaft assembly 54 and push rod 55.

In the embodiment shown, the apparatus will maintain a partial vacuum of about −22 inches of mercury therein which substantially prevents incorporation of air into the mixture during mixing and transfer to the cartridge.

The operator can now rotate the handle 70 (FIG. 3) in either or both directions (clockwise and counterclockwise) to start mixing of the monomer and polymer. When the monomer and polymer are mixed under partial vacuum, as here, the void volume of the resultant high molecular weight polymeric material is considerably less than when mixed in air at atmospheric pressure.

The conical funnel geometry of the funnel 30 minimizes edges and discontinuities in the flow stream lines of the cement as it is being mixed. Since the object of the mixing and transfer device embodying the invention is to minimize voids and pores in the resultant cement mixture, any discontinuities in the stream lines of the mixture during the transfer operation could cause turbulence or eddies. Therefore, voids or pores could be introduced into the cement mixture at such discontinuities. Accordingly, this problem is avoided by the funnel-shaped geometry of the mixing chamber 11.

During mixing, the flexible auger 81 contacts the inside surface of the conical funnel 30 along its outermost edge as it rotates about the central axis of the bowl. The auger 81 serves two purposes. First, during the mixing operation, if rotated top edge leading (here clockwise seen from above), the auger moves cement from the upper region of the cone-shaped funnel 30 down into the lower region of such funnel. The auger thus continuously brings down powder loose in the upper portion of the funnel 30 down into contact with the mixture at the bottom of the funnel. The highest concentration of the liquid monomer (particularly when the monomer is put into the funnel first) may be at the bottom of the funnel 30. The highest concentration of the powder, which is relatively lightweight, may be expected in the upper region of the funnel 30, particularly when the powder is added to the funnel after the liquid monomer. Therefore, the auger aids the mixing process by continuously moving powder downward into the highest concentration of monomer. Second, during the transfer operation hereafter described, the auger moves the mixture off the conical sidewall 31 of the funnel 30 and out the bottom of the funnel 30 into the open top of the cartridge 12.

During mixing, the auger 81 and paddle 82 cooperate in a unique manner. The springy metal auger 81 at its radially outermost edge attacks the conical sidewall 31 of the funnel 30 during mixing and wipes material off it. The paddle 82 maintains a gap, for example between ⅛ inch and ¼ inch, radially in from the conical sidewall 31 of the funnel 30 and thereby spreads a thin film of cement and cement components along the peripheral conical wall 31 of the funnel 30. The thin film is created to further assist in deaerating the cement, take the air out of it, by reason of exposure of the surface of this thin film to the partial vacuum within the funnel 30. The auger 81 thereafter rotatably scrapes that thin film of cement material back down into the center of the mix. The auger continues to tend to keep moving the highest concentration of powder down into the highest concentration of monomer in the mix.

The central opening 95 (FIG. 3) in the auger 81 provides additional edges to contact the cement materials to be mixed and help mix same. The central opening 95 also allows the auger 81 as a whole to be more easily flexed and to conform at its outer edge 91 more closely to the inner face of the conical funnel sidewall 31 during mixing and transfer.

It is important that the feather seal 146 of the piston be effective to allow the piston to form a positive blockage at the bottom of the mixing funnel 30 since otherwise the monomer liquid would tend to run down into the bottom of the cartridge, prior to mixing, and perhaps even into the bottom of the vacuum shroud, thereby preventing proper mixing and production of a proper bone cement.

It is important that, during mixing, the piston be kept in its uppermost position shown in FIG. 3A and FIG. 3 by the retention or detent structure shown at 150, 151 in FIG. 3A. With the piston thus held in a position closing the bottom of the conical sidewall 31 of the mixing funnel 30, the solid and liquid components to be mixed are kept within the funnel 30. This keeps the cement components to be mixed in contact with the paddle 82 and auger 81 by which they are mixed and also keeps such components facing upward into the partial vacuum in the funnel over a wide surface area, much wider than would be possible if the components were mixed within the cartridge 12, so as to increase the opportunity for deaeration at the top surface of the mixture.

Using the funnel-shaped mixing chamber 11 here disclosed, it is possible to make larger batches of bone cement than has normally been the case in the past. A typical conventional cement batch is about 60 grams and the mixing chamber 11 of the present invention handles easily 3 times that, the total volume of the mixing chamber 11 being about 550 cubic centimeters.

After a minute or two of initial mixing, the mixed cement is the consistency of thin pancake batter. The mixing time is typically 30 to 90 seconds whereupon the mixture is transferred down into the cartridge.

After sufficient mixing, the mixed cement is transferred down to the cartridge 12 as follows. First, the operator radially pulls outward the retaining clip 113, out of contact with the push rod 55 and handle 70. This unlocks the push rod 55 and allows the operator to manually push it downward from its FIG. 3 to its FIG. 4 position. The thus downward moving bottom of the rod element 100 (FIG. 3A) will, after a slight lost motion, contact the top of the piston 140 (here at the upward facing surface of the depression 142, overcoming the detent 150, 151 (FIG. 3A) and downwardly displacing the piston almost entirely out of the bottom end of the mixing chamber 11 and entirely or almost entirely into the open top end of the cartridge tube 124.

Again then, after a minute or two of mixing, the cement is typically in the form of a heavy but quite flowable, syrup-like or thin batter-like liquid. Such liquid by its weight tends to push the piston 140 down further in the cartridge 12. Such gravitational transfer of the mixed liquid cement downward into the cartridge is assisted by operator rotation of the handle 70 in a direction such that the top edges 93 and 94 of the auger 81 and paddle 82 circumferentially advance ahead of the bottoms thereof (the auger 81 and paddle 82 being tilted as seen in FIGS. 5 and 5B). The auger 81 and paddle 82 thus tend to wedge downwardly the portions of the mixed cement lying directly circumferentially ahead thereof as they rotate in the funnel 30. In any event, by means of gravity and this wedging action, the flowable mixed cement drops downward into the open top of the cartridge and displaces downward the piston 140 from its intermediate dotted line position of FIG. 4 toward and possibly (if enough cement is mixed) to its bottom-most solid line position of FIG. 4.

Downward escape of the piston 140 out of the bottom of the cartridge tube 124 is positively blocked by the internal flange 127 in the bottom of the tube 124. Note that both the mixing of the cement components and the transfer of the mixture from the mixing chamber 11 into the dispensing cartridge 12 takes place entirely within a partial vacuum. This avoids incorporation of air into the cement mixture during mixing and also during transfer into the cartridge and so avoids unwanted porosity of the cement.

The vacuum release label is most easily an adhesive bottomed paper or plastic film tape like a conventional household adhesive tape, which sticks to the top of the lid horizontal wall 46 and blocks the hole 155 thereby preventing leakage of air into the interior of the apparatus through such hole.

Figure 4:
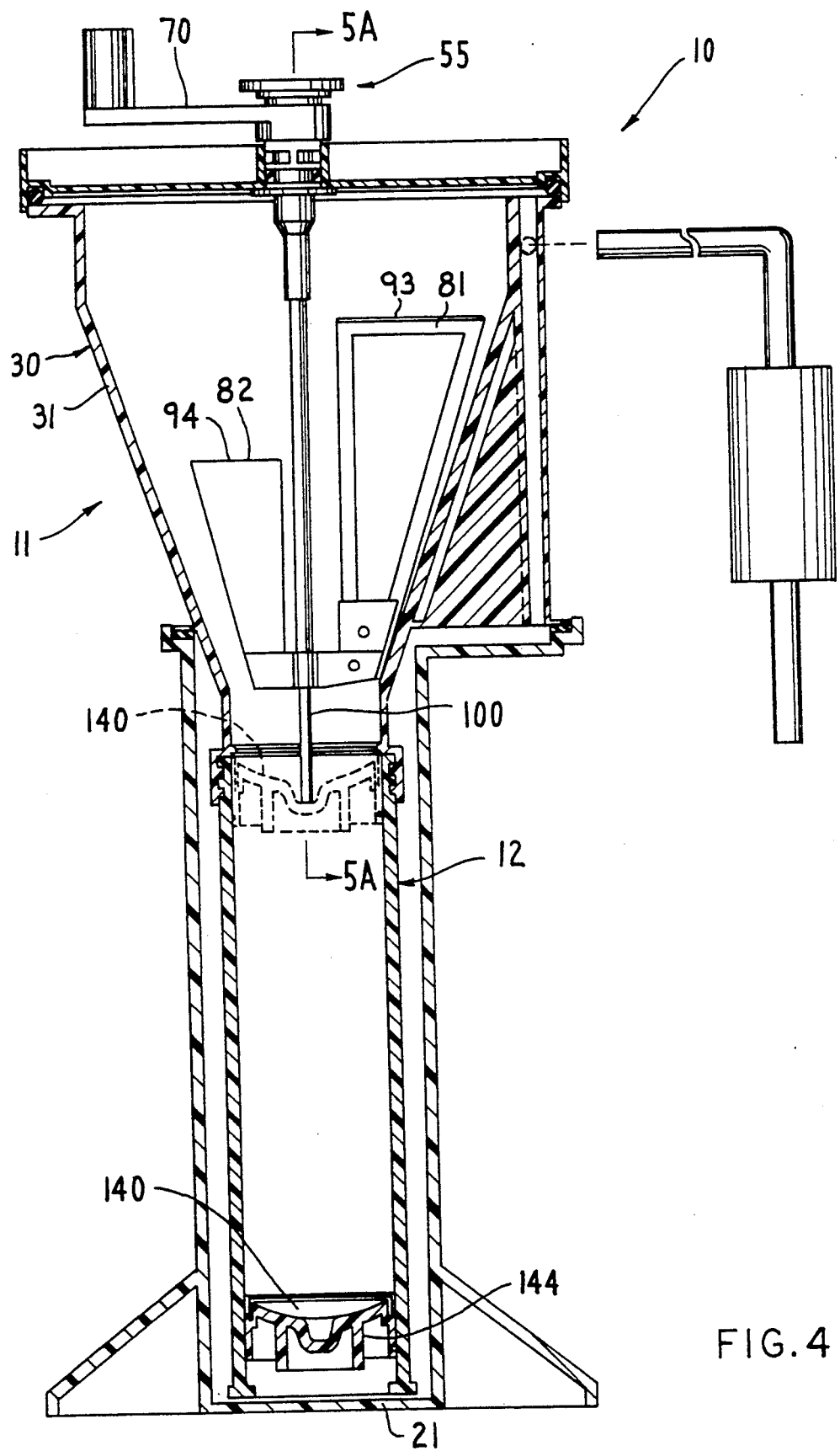
FIG. 4 is a view similar to FIG. 2 but with the piston and push rod in respective downward positions.

On the other hand, when mixing is completed and the mixture has been transferred into the cartridge 12, filling the cartridge and pressing the piston 140 down to its bottom FIG. 4 position, such that it is now desired to remove the filled cartridge from the apparatus 10, the tape or label 156 can be manually lifted off the lid 45 and discarded, allowing air to bleed through the hole 155 in the lid and return the mixing chamber 11 and vacuum shroud 13 and cartridge 12 to atmospheric pressure in the interior thereof. At the same time vacuum source VS can be disconnected from the apparatus, as by disconnecting the vacuum tube 38 from the stub 37 on the mixing chamber 11.

With the vacuum thus released, the mixing chamber 11 can then be lifted off the top of the vacuum shroud 13, drawing up with it the filled cartridge 12. The top of the cartridge can then be unscrewed from the threaded connection sleeve 121 at the bottom of the mixing chamber 11 and the mixing chamber 11 can be discarded. The vacuum shroud 13 can be retained for later use with a new mixing chamber 11, etc. for mixing a new batch of cement at some time in the future.

The filled cartridge 12 (FIG. 2) can then have a suitable output nozzle 131 threaded on the threads 126 at the upper end thereof and the cartridge as a whole, with nozzle 131, can be mounted on a gun (not shown) of the kind above discussed, to advance the piston away from the flange 125 and toward the threads 126 to press the mixed cement through the nozzle 131 into a desired bone cement location, such as, for example, the upper end of a femur where injected cement is to receive and fixedly hold in place the lower tang of a conventional hip joint replacement.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An apparatus for mixing bone cement and containing the mixed bone cement preparatory to dispensing, the apparatus comprising:

a mixing chamber having means therein for mixing components to form bone cement and means defining an outlet for outputting mixed cement;

a cartridge having means defining an inlet releasably coupled to the outlet of said mixing chamber for receiving mixed bone cement therefrom;

a piston having a starting position sealing the outlet of mixing chamber from communication with the inlet of the cartridge, said piston being snugly and sealingly slidable in and along said cartridge away from the outlet of said mixing chamber and ahead of mixed cement therefrom;

retention means for resiliently holding said piston with respect to said mixing chamber and cartridge in said starting position;

a rod mounted for longitudinal movement in said mixing chamber and having an end releasably engageable with said piston for advancing said piston out of said starting position and past said retention means and along said cartridge in response to movement of said rod beyond said mixing chamber outlet, to allow mixed cement to enter the cartridge behind the piston.

2. The apparatus of claim 1 including a hollow rotatable shaft in said mixing chamber, in which said piston has a central recess for receiving said end of said rod to thus help pilot said hollow shaft upon rotation thereof.

3. The apparatus of claim 1 including a hollow shaft mounted for rotation in said mixing chamber, said rod being coaxially housed in said hollow shaft, said hollow shaft carrying said cement mixing means rotatable thereby to mix cement in said mixing chamber.

4. The apparatus of claim 1 in which said rod has means to seal and prevent air from entering said mixing chamber along said rod throughout the range of travel of said rod.

5. The apparatus of claim 1 in which said retention means comprises a one way snap connection means (1) requiring a force to dislodge the piston from said starting position toward a central portion of the cartridge which is greater than the force to move the piston along the central portion of said cartridge and (2) positively blocking movement of the piston into a central portion of the mixing chamber.

6. An apparatus for mixing bone cement and containing the mixed bone cement preparatory to dispensing, the apparatus comprising:

a mixing chamber having (1) inlet means for receiving components to be mixed and (2) means therein for mixing components to form bone cement and (3) an outlet for mixed cement;

a cartridge having an inlet releasably coupled to the outlet of said mixing chamber for receiving mixed bone cement therefrom;

a piston snugly and sealingly slidable (1) from a starting position sealing the outlet of said mixing chamber from communication with said cartridge, (2)

along the interior of said cartridge toward a remote end of said cartridge;

a rod mounted for longitudinal movement in said mixing chamber and having an end releasably engageable with said piston for pushing said piston out of said starting position and along said cartridge in response to movement of said rod beyond said mixing chamber outlet, to allow mixed cement to enter the cartridge.

7. The apparatus of claim 6 in which said mixing chamber is atop said cartridge, said piston having a concave rounded upper end facing up into a bottom part of said mixing chamber and further having an annular feathered perimeter edge upward and outward angled to resiliently lay against and smoothly continue an inner surface of said bottom part of said mixing chamber to provide said mixing chamber with a sealed rounded bottom and to wipe sealingly against the interior surface of said cartridge as said piston is moved downwardly therein for loading, and upwardly therein for unloading, of mixed cement.

8. The apparatus of claim 6 in which said mixing means includes means in said mixing chamber for moving cement from an upper region of said mixing chamber down into a lower region thereof to mix same and for moving such mixed cement off an inner surface of said mixing chamber and into said cartridge atop said piston, said means for moving including a flexible auger mounted for rotation about a central axis of the mixing chamber and having a sloped outer edge contacting said inner surface of said mixing chamber.

9. The apparatus of claim 8 in which said means for moving also includes a hollow central shaft containing said rod and rotatably mounted in said mixing chamber for rotation about said central axis and on which said auger is fixed, said means for moving also including a paddle fixed on said central shaft and circumferentially offset from said auger.

10. The apparatus of claim 9 in which said auger comprises a resilient plate fixed at its bottom to said central shaft, said auger having a radially inner edge parallel to and spaced form said central shaft and a radially outboard edge diverging upward therefrom, the center of said auger being an opening of shape corresponding to the outer perimeter of said auger, said paddle having radially inner and outer edges respectively adjacent said central shaft and spaced radially rom the inner surface of said mixing chamber.

11. The apparatus of claim 6 in which said means for mixing comprises a hollow central shaft containing said rod and having a vane-like mixing element fixed thereon for rotation adjacent a perimeter wall of said mixing chamber, a lid closing the top of said mixing chamber and rotatably supporting said hollow central shaft pendently therefrom, and central means on said piston and rod for piloting the bottom of said rod and thereby the bottom of said hollow central shaft with respect to said piston and for rotation of said mixing element with respect to said mixing chamber.

12. The apparatus of claim 6 including a vacuum shroud surrounding said cartridge and at least extending up substantially to said mixing chamber, and means for connecting a vacuum source to the interior of said mixing chamber and vacuum shroud to keep said mixing chamber and cartridge at a subatmospheric pressure during cement mixing and loading of the mixed cement into said cartridge.

13. The apparatus of claim 12 in which said mixing chamber comprises an open topped, downwardly converging funnel like sidewall with a radially outwardly extending top flange, said mixing chamber further comprising a horizontal lid and an annular seal separating said lid from said top flange and creating a vacuum seal therebetween, said means for connecting to a vacuum source comprising a passage outside said mixing chamber sidewall and opening up through said radially outward extending top flange of said mixing chamber at a location radially inboard of said annular seal, with the top of said passage being spaced below said lid for communication between said passage and the interior of said mixing chamber.

14. The apparatus of claim 13 including a vacuum release hole in the lid, a closure normally covering and sealing said hole and being removable to release vacuum from said mixing chamber and vacuum shroud.

15. The apparatus of claim 14 in which said vacuum shroud has a closed bottom and a radially outward extending bottom portion for supporting, in a stable manner, said mixing chamber and cartridge in an upright position.

16. The apparatus of claim 6 including means for permitting release of said cartridge inlet from said mixing chamber outlet after loading of mixed cement into said cartridge said piston having seal means engageable with the interior of said cartridge, said piston having end means facing toward said remote end of said cartridge and engageable for causing said piston to push said loaded mixed cement back toward and eject same out of said inlet of said cartridge, nozzle means fixable on said inlet of said cartridge in place of said mixing chamber for directing bone cement ejected from said cartridge inlet to a surgical site.

* * * * *

UNITED STATES PATENT AND TRADEMARK OFFICE
CERTIFICATE OF CORRECTION

PATENT NO. : 5,265,956
DATED : November 30, 1993
INVENTOR(S) : Charles L. NELSON et al It is certified that error appears in the above-identified patent and that said Letters Patent is hereby corrected as shown below:

Column 15, line 42; change "form" to ---from---.
           line 48; change "rom" to ---from---.
Column 16, line 43; after "cartridge" insert ---,---.

Signed and Sealed this

Thirty-first Day of January, 1995

*Attest:*

BRUCE LEHMAN

*Attesting Officer*      *Commissioner of Patents and Trademarks*